United States Patent [19]

Collins et al.

[11] Patent Number: 4,643,547

[45] Date of Patent: Feb. 17, 1987

[54] OPHTHALMIC INSTRUMENT SUPPORT

[75] Inventors: Ronald J. Collins, Fort Wright, Ky.; Michael Cain, North Andover, Mass.

[73] Assignee: Dentsply Research & Development Corp., Milford, Del.

[21] Appl. No.: 664,832

[22] Filed: Oct. 25, 1984

[51] Int. Cl.⁴ ........................ A61B 3/00; A47B 11/00
[52] U.S. Cl. .................................. 351/245; 108/139; 108/140; 312/235 R
[58] Field of Search .............................. 351/244, 245; 248/280.1, 283; 108/139, 140, 141, 142, 143; 312/235 R, 21–27

[56] References Cited

U.S. PATENT DOCUMENTS

| | | |
|---|---|---|
| 978,299 | 12/1910 | Jacobs . |
| 1,272,015 | 7/1918 | Davis .................................. 108/141 |
| 1,287,955 | 12/1918 | Gay .................................... 108/141 |
| 1,494,666 | 5/1924 | Clement . |
| 2,149,141 | 2/1939 | Hunsicker . |
| 3,201,795 | 8/1965 | Cuppers et al. . |
| 3,572,913 | 3/1971 | Korh et al. . |
| 4,421,394 | 12/1983 | Schon et al. . |

*Primary Examiner*—Rodney B. Bovernick
*Assistant Examiner*—P. M. Dzierzynski
*Attorney, Agent, or Firm*—C. Hercus Just; E. J. Hanson, Jr.

[57] ABSTRACT

An ophthalmic instrument support having a flat floor-supported base and a cabinet extends upward from one end of the base, a post projects upward from the cabinet and the upper end of the post pivotally engages one end of a horizontal frame upon which a table is mounted for limited horizontal movement to permit a pair of spaced instruments thereon selectively to be brought into alignment with the eyes of a patient when seated in a vertically adjustable chair with the patient's lap extending beneath the horizontal frame. The post is adjustable vertically a limited amount to dispose the table and instruments thereon at a desired vertical position according to a doctor's eyes when the doctor is seated upon another chair opposite a patient. Positioning recesses and detents releasably maintain the table in longitudinally adjusted positions upon the frame, and an actuating member for an electric switch is mounted beneath the portion of the table which extends over the lap of a patient and is operable to stop elevating a patient in the adjustable chair when the lap or legs of a patient engage the actuating member while being elevated by the chair.

5 Claims, 7 Drawing Figures

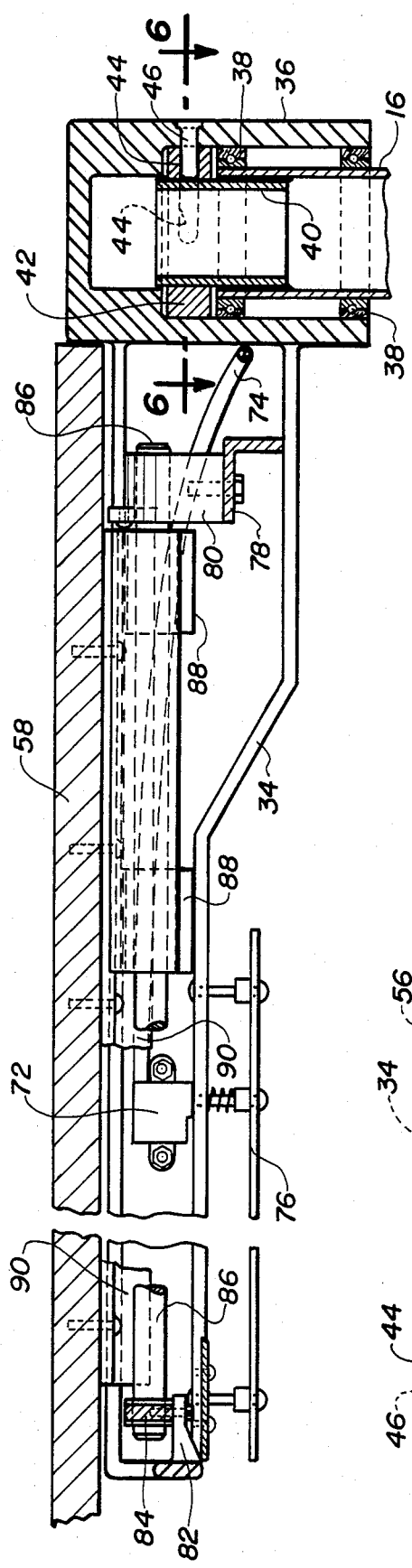
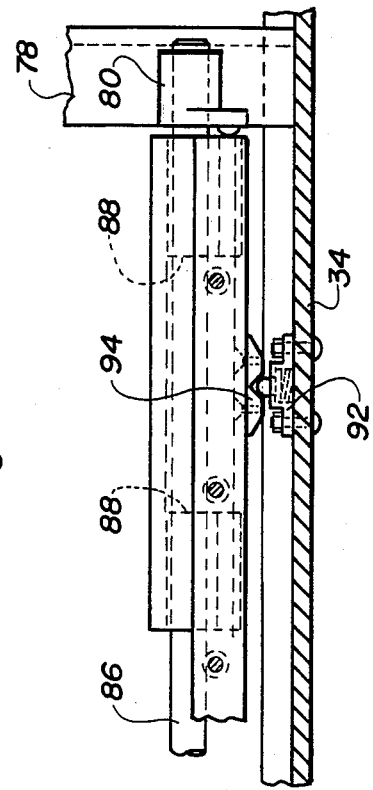
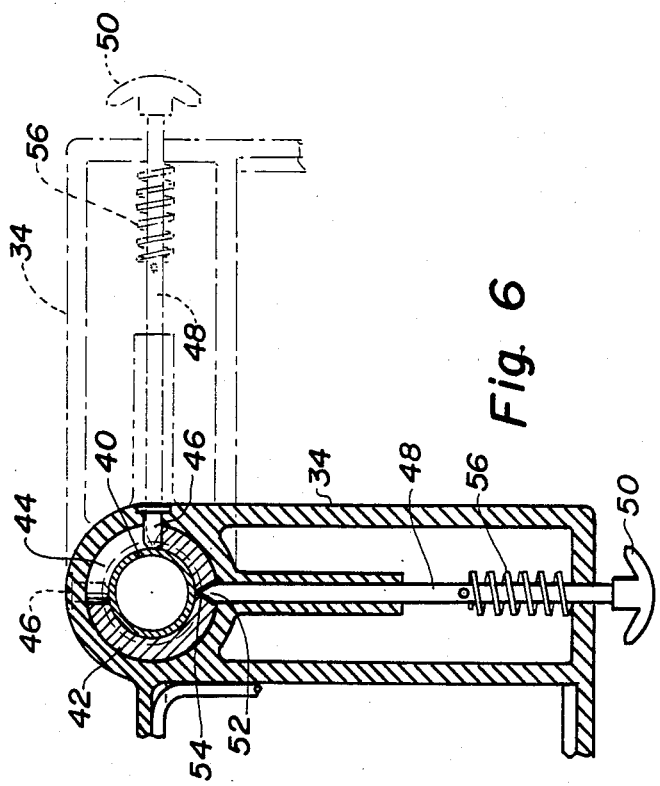
Fig. 5
Fig. 7
Fig. 6

OPHTHALMIC INSTRUMENT SUPPORT

BACKGROUND OF THE INVENTION

Ophthalmic stands of various kinds have been used by ophthomologists for many years. Prior to the present time, it was common practice to arrange different instruments and examination chairs or stools at different locations in an operatory. This required both the doctor and the patient to move to such locations and resulted in interruptions in the examination of a patient and also was time-consuming.

In more modern practice of ophthomology, it is more common for both the doctor and patient to remain in chairs which are substantially in fixed positions in the operatory opposite each other and respective to a number of the examination instruments movable to and away from the patient. To accomplish this it is possible to mount a number of different instruments on a post upstanding from a suitable base and of which prior U.S. Pat. No. 1,494,666 to Clement, dated May 20, 1924 is an examaple of an older type, and prior U.S. Pat. No. 2,149,141 to Hunsicker, dated Feb. 28, 1939, shows a further variation of another older type.

Prior U.S. Pat. No. 3,201,795 to Cuppers et al, dated Aug. 17, 1965, illustrates a still further effort at consolidating examination instruments available at a single position of both doctor and patient and in which different instruments are brought into operative position by rotating an arm assembly to which the instruments respectively are connected.

A still more recent proposal comprises the subject matter of prior U.S. Pat. No. 3,572,913 to Korh et al, dated Mar. 30, 1971, in which a circular arrangement of instruments is movable around a patient seated in a stationary chair.

It now has become popular to support ophthalmic examination instruments upon a horizontal table supported by a cabinet-like base from which a post projects to support certain instruments, while others are supported upon the table which is positionable over the lap of a patient seated upon a chair which, for example, can be raised and lowered to adjust the height of a patient relative to the eyepieces of certain instruments. Prior U.S. Pat. No. 978,299 to Jacobs, dated Dec. 13, 1910, shows an example of the first type and U.S. Pat. No. 4,421,394 to Schon et al, dated Dec. 20, 1983, shows an example of the second type.

SUMMARY OF THE INVENTION

It is among the principal objects of the present invention to provide an ophthalmic instrument stand offering maximum comfort to a patient and minimum need to change position either by the doctor or patient during an examination of a patient's eyes by adapting improvements in the structure and use of a stand having an over-the-patient table on which a plurality of instruments are mountable in side-by-side relation and the table is shiftable to present one or the other of the instruments opposite a patient and doctor and, in regard to which, the patient is seated on a chair at least partially beneath the table and the chair is capable of vertical movement to dispose the eyes of the patient in line with the instruments.

Another object of the invention is to support the table for vertical adjustment to set it at a vertical position with instruments thereon adjusted relative to the doctor's eyes for all uses of the instruments on the table and, for the ease of use of the table by the patient, the table is supported for limited rotation in a horizontal plane, of about 90° around the axis of a post on which the table is supported, the table being selectively disposable in an operative or an access or exit position relative to a patient.

A further object of the invention is to provide a horizontal frame beneath the table and upon which the table is supported for limited movement longitudinally therealong in opposite directions to dispose instruments thereon selectably in spaced operative positions as aforesaid, and also provide on said frame adjacent the lower surface thereof, a switch operating member adapted to be connected to a switch or power means for the chair for the patient which is adapted to be raised and lowered while a patient is seated thereon, said actuating member being engageable by the lap or knees of a patient when being elevated in the chair beneath said frame and thereby stop further elevating movement of said chair.

Details of the foregoing objects and of the invention as well as other objects thereof are set forth in the following application and illustrated in the accompanying drawings comprising part thereof.

DESCRIPTION OF THE DRAWINGS

FIG. 5 is a fragmentary longitudinal section taken on the line 5—5 of FIG. 2.

FIG. 6 is a fragmentary horizontal section taken on the line 6—6 of FIG. 5.

FIG. 7 is a fragmentary illustration of details as seen on the line 7—7 in FIG. 4.

DETAILS OF THE PREFERRED EMBODIMENTS OF THE INVENTION

Figure 1:
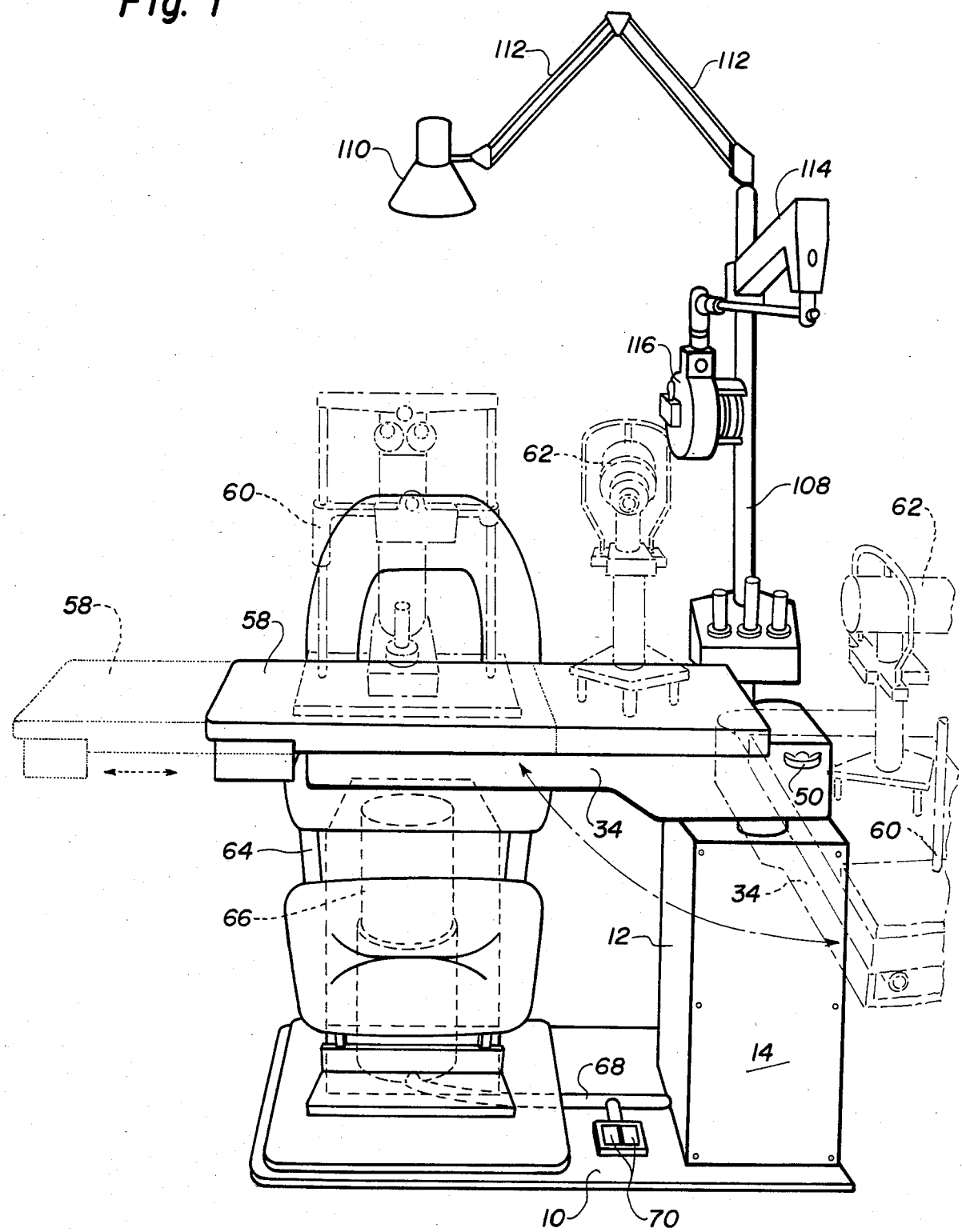
FIG. 1 is a perspective view showing an ophthalmic instrument support embodying the principals of the invention and illustrating one position of the support means in full lines, and an alternate position thereof in phantom.
Figure 2:
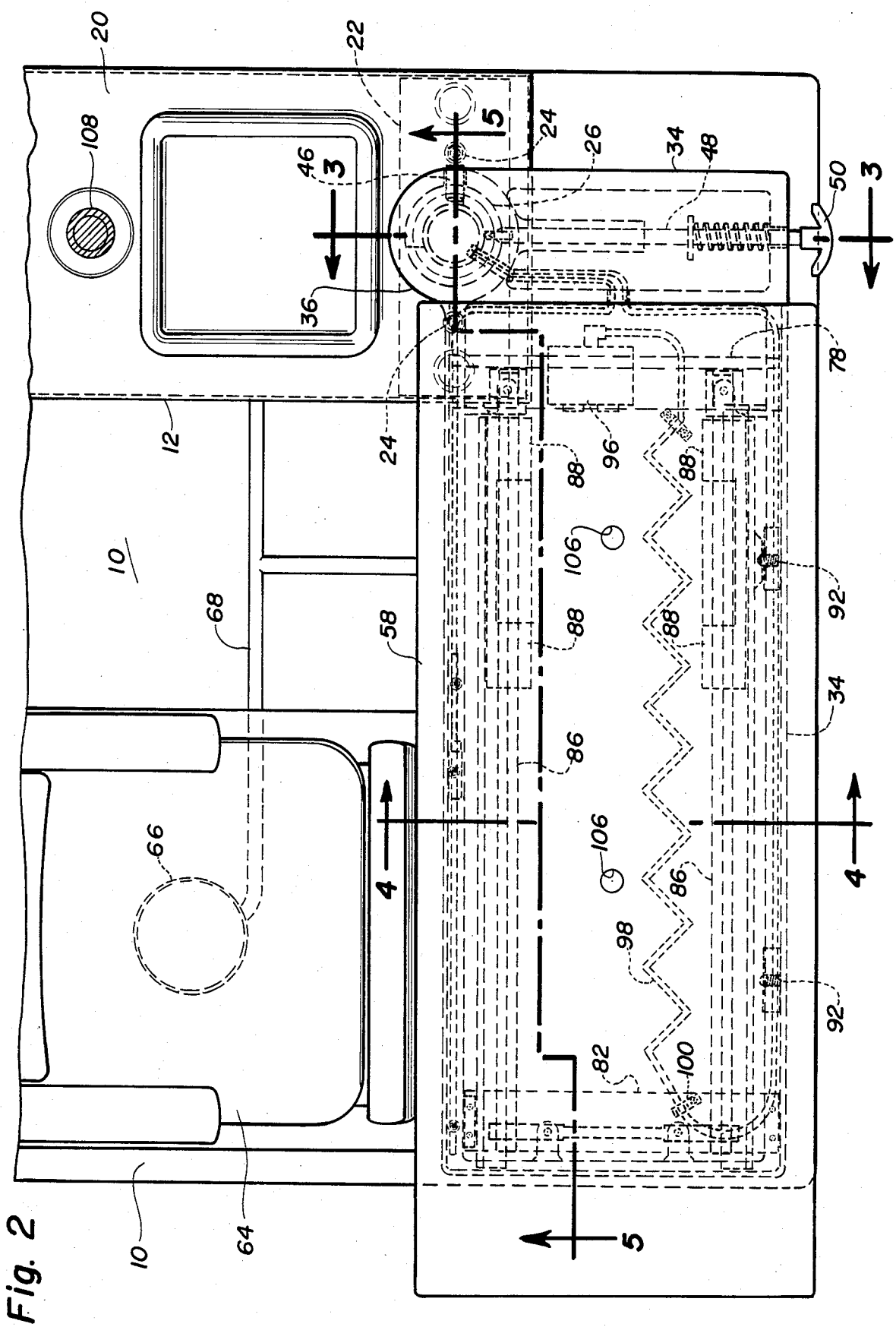
FIG. 2 is a fragmentary plan view of the top of the table and cabinet shown in FIG. 1 as well as a fragmentarily illustrated portion of a chair for a patient adjacent one side of the table.

Referring especially to FIGS. 1 and 2, it will be seen that the invention comprises a flat base 10 adapted to be placed upon a suitable support such as the floor of an operatory. Upstanding from one end of the base is a cabinet 12 having a removable front cover 14 to permit access to the interior thereof. Extending upward from the cabinet 14 is a vertical tubular post 16 which extends through an opening 18 in the top 20 of the cabinet.

Figure 4:
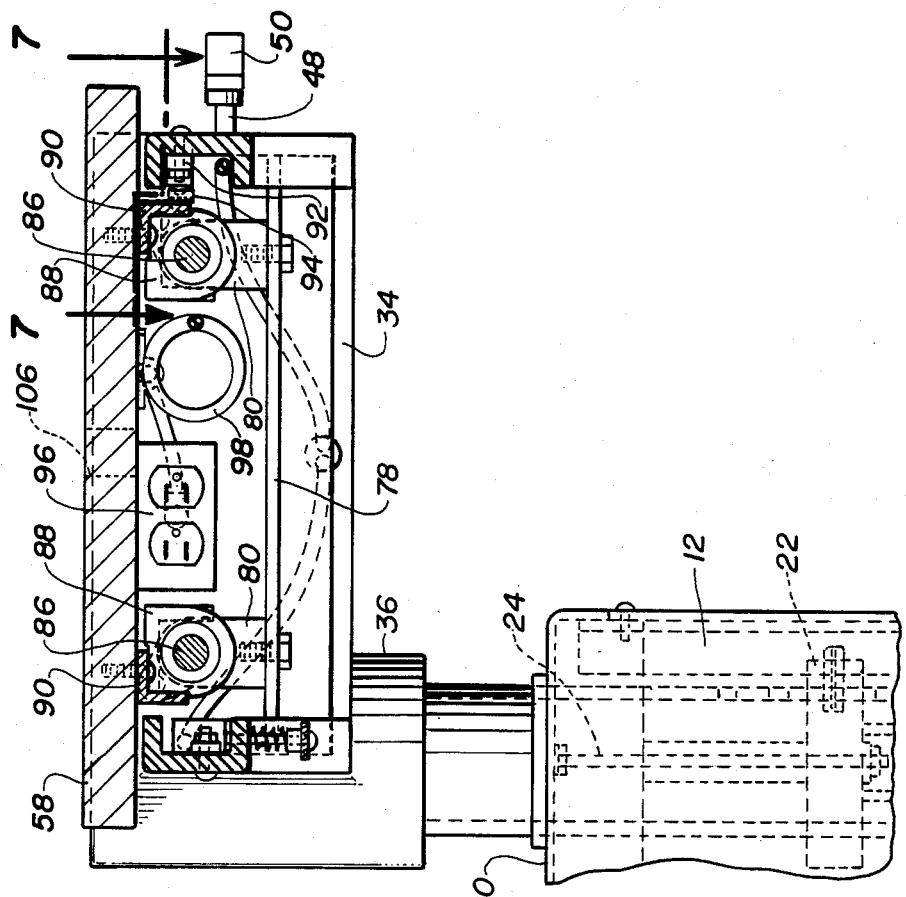
FIG. 4 is a fragmentary vertical sectional view taken on the line 4—4 of FIG. 2.
Figure 3:
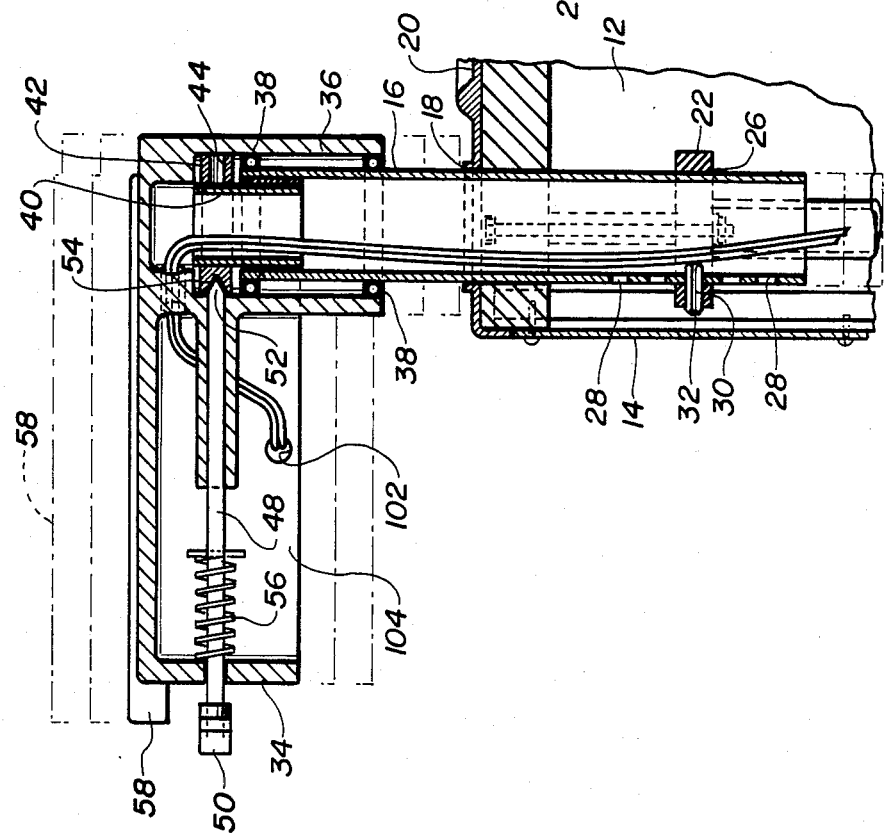
FIG. 3 is a fragmentary vertical sectional view taken on the line 3—3 of FIG. 2.

A heavy horizontal plate 22 is shown in phantom in FIGS. 2 and 4 and in full lines in FIG. 3. Said plate is supported by a pair of vertical rods 24 the upper ends of which are connected to the top 20 of cabinet 12. The plate 22 is also provided with a central bore 26 through which the lower portion of the post 16 extends, whereby, between the opening 18 and bore 26, the post is amply supported against tilting movement. The post 16 also is supported by limited vertical adjustment by being provided with a vertical row of evenly spaced locking apertures 28 selectively adapted to be transversely aligned with another transverse opening 30 in plate 22 for purposes of receiving a locking pin 32 which commonly extends through the opening 30 and the selected aperture 28 in post 16.

The upper end portion of post 16 supports a horizontal frame 34, which preferably is a casting of metal, and at one end is provided with a large socket 36 which receives the upper end of post 16 for limited rotation about the axis of the post. Suitable anti-friction bearings 38 are disposed between the inner wall of the socket 36 and the exterior surface of post 16, said bearings being in vertically spaced relationship to prevent tilting of the frame 34 from a normal horizontal position and permit ready rotation of the frame about the axis of post 16.

Referring to FIG. 5, it also will be seen that the upper end of post 16 has a tubular extension 40 fixed securely thereto, by welding or otherwise, and the portion thereof which projects above the upper end of post 16 has a circular collar 42 suitably fixed thereto, and said collar is provided with an arcuate groove 44 which is best shown in FIG. 6 but also is seen in FIGS. 3 and 5. In FIG. 5, it will also be seen that a rotation control pin 46 extends through the wall of socket 36 to control movement of frame 34 through a 90° arc between the respective positions, shown in full lines and phantom in FIG. 6, for purposes of limiting the swing of the frame 34 between the operative position shown in FIG. 1 and the phantom access or exit position shown therein. A further function of the pin 46 is to prevent accidental upward removal of the socket 36 from the upper end of post 16.

Additional control means for maintaining the frame 34 in either the full line, operative position shown in FIG. 1 and the phantom access or exit position shown therein, comprises manually operated elongated rod or pin 48 which has a manually engageable knob 50 on the outer end thereof, the inner end of pin 48 having a point 52 which, when the frame 34 is in the full line position shown in both FIGS. 1 and 6, is disposable in a notch or recess 54 which is complementary to the shape of the point 52, said recess being formed in collar 42 which is fixed relative to post 16. Thereby, the pin 48 will positively retain the frame 34 in the operative position shown in full line in FIG. 1.

To pivot the frame from the operative position to the access or exit position shown in phantom in FIG. 1, it is necessary to withdraw the pin 48 by operation of knob 50, against the action of compression spring 56. When the frame 34 reaches the phantom position shown in FIGS. 1 and 6, the rotation control pin 46 will have moved to the phantom position shown in FIG. 6, whereby the point 52 of pin 48 can be received within the end of the arcuate groove 44 from which the rotation control pin 46 has moved, thereby providing means to positively retain the frame 34 in the access or exit phantom position shown in FIGS. 1 and 6.

As can be seen from FIG. 1, there is a table 58 mounted upon the frame 34 for longitudinal movement between at least two positions respectively shown in phantom and full line illustrations in FIG. 1. The table functions to support, for example, at least two different examination instruments 60 and 62 which are shown in phantom in said figure. In the use of said instruments, a patient is seated upon the examination chair 64. From FIG. 1, it will be seen that the instrument 60 is in line with the chair 64. When the instrument 62 is to be used, it is only necessary to longitudinally shift the table 58 to the phantom position shown in FIG. 1 and thereby dispose instrument 62 in line with chair 64. Chair 64 also preferably is of the type that can be moved vertically in opposite directions by suitable power means 66 in the base of the chair, the power being supplied from appropriate means of any conventional type, for example, suitable to be contained within the cabinet 12. Power line 68 extends between the power means 66 and the power supply within cabinet 12 and operation of the power means is controlled by up and down foot switches 70, for example, shown in FIG. 1.

It will be understood that when the overall unit of the invention is installed in an operatory, it will be assumed that an examining doctor will be seated in another chair or stool opposite the chair 64. The doctor's chair preferably is not vertically adjustable and, therefore, in order to adjust the instruments for the eyes of the doctor, the frame 34 upon which the table 58 is mounted will be vertically adjusted to a suitable position of which several examples are shown in phantom in FIG. 3. The most suitable position for a specific doctor is determined and is stabilized by inserting the locking pin 32 in one of the locking apertures 28 corresponding to the desired position for the doctor. Thereafter, during operation by a specific doctor, the vertical position of the table 58 remains fixed and therefore, it is necessary to vertically adjust the position of a patient by operating the power means 66 in the base of chair 64 to bring the patient's eyes in line with the instruments being utilized upon the table 58.

Referring to FIG. 5, for purposes of providing safety in elevation of the seat of the chair 64 and the patient in it, a safety switch 72, see FIG. 5, is supported upon the frame 34 and by an appropriate circuit conduit 74, is connected in the control means for the power supply element in the cabinet 12, for example. Safety switch 72 is operated by a plate-like actuating member 76 which normally is spring pressed downwardly. In the normal position of the patient with respect to table 58, either the lap of the patient or thighs and or knees of the patient are disposed below actuating member 76. In the event the seat of the chair 64 is accidently elevated to a higher position than is intended, at least part of the leg or the lap anatomy of the patient will contact member 76 and open the switch 72 to immediately stop operation of the power means, following which actuation of the foot switches 70 may be effected to lower the patient to a desired operating elevation with respect to instruments 60 or 62, for example.

As indicated above, the table 58 is longitudinally moveable with respect to the elongated frame 34. Referring to FIGS. 4 and 5, it will be seen that frame 34 has a transverse member 78 which supports a pair of brackets 80 and, at the outer end of frame 34, another transverse member 82, fixed to frame 34, supports additional bracket members 84. Extending between and supported by the brackets 80 and 84 are a pair of parallel guide rods 86 upon which a pair of guide bearings 88 are longitudinally moveable, the guide bearings being connected to angle support members 90, for example, horizontal flanges on said angle members being afixed by screws or bolts to the lower surface of the table 58 as best shown in FIG. 4.

Movement of the table 58 with respect to frame 34 is effected manually and, for convenience as well as safety, frame 34, along one longitudinal side thereof, is provided with a pair of spring-pressed detents 92, see FIGS. 2 and 7, which are spaced longitudinally in accordance with the distance between the centers of instruments 60 and 62, for example, or in any other spacing which may be desired. The detents 92 coact with a positioning notch member 94, see FIGS. 2 and 4, which receives one of the detents 92 when the table is positioned, for example, either in the full line or phantom positions respectively shown in FIG. 1.

Table 58, on the under side thereof, at the end nearest the socket 36 on frame 34, is provided with an electric outlet 96, see FIGS. 2 and 4, into which one end of a coiled expansible and contractible conduit 98 is connected. An intermediate portion of the conduit is connected by clip 100 to the other end of frame 34 and, from there, said conduit extends back toward the end of the frame on which socket 36 is mounted and passes through a hole 102 in web 104 of frame 34, see FIG. 3, and from there the conduit 98 extends down the interior of post 16 to a source of electric energy. The electric outlet 96 is for purposes of having conduits from any of the examining instruments, such as 60 and 62 shown in FIG. 1, connected thereto. For access to the outlet 96, the table is provided with exemplary passages in the form of holes 106 in the table top as shown in FIG. 2 and also in phantom in FIG. 4.

For purposes of accommodating additional examining instruments as well as a light, referring to FIG. 1, it will be seen that an additional vertical post 108 is supported at its lower end by cabinet 12, the post 16 extending upward from the top 20 thereof. A light 110, supported upon adjustable arms 112 is attached to the upper end of post 108 as shown in FIG. 1. In addition, a lateral arm 114 is adjustable vertically upon post 108 for supporting an additional instrument 116, such illustrations being exemplary for purposes of showing the versatility of the entire examination system comprising the present invention.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

It is claimed:

1. An ophthalmic instrument support comprising in combination, a base positionable upon a floor surface for support, a horizontal frame having one end supported by the upper end of said post, an elongated table slidably supported upon the top of said frame for limited longitudinal movement, said table being adapted to support several instruments upon said table in longitudinally spaced positions thereon, whereby longitudinal movement of said table permits selective positioning of said instruments in alignment with a patient when seated upon a chair positioned adjacent one edge of said table, an electric outlet mounted beneath said elongated table, an electric conduit having an expandable and contractable portion extending between said outlet and the end of said frame farthest from said outlet and fixed respectively thereto, the end of said conduit adjacent said outlet being secured thereto and the opposite end thereof being connectable to a source of electric current, whereby any electric means requiring current on said instruments may be connected to said electric outlet and be supplied with current therefrom regardless of which instrument is positioned in front of a patient, an electrically operated means operable to elevate the seat of a chair positioned adjacent one edge of said frame and table, an electric circuit connected between said electrically operated means and said aformentioned source of current, a safety switch also in said circuit, and an actuating member for said safety switch supported by said frame below the lower surface thereof in a location to be engaged by the lap or thighs of a patient when seated in said chair and said lap or thighs being at least partially beneath said frame and table, thereby to discontinue any further elevation of a patient seated within said chair when said member is so engaged by said lap or thighs of said patient.

2. The support according to claim 1 in which said actuating member for said safety switch comprises a substantially flat plate supported beneath the portion of said frame which extends over a patient's lap or thighs, said plate having a length sufficient to extend across at least one thigh or knee of a patient, and spring means between said plate and frame operable to space said plate away from the lower portion of said frame and operable normally to maintain the safety switch in open position to interrupt the supply of current to said electrically operated means.

3. An ophthalmic instrument support comprising in combination, a base positionable upon a floor surface for support, a post extending upward from said base, a horizontal frame having one end supported adjacent one end by the upper end of said post and extending laterally therefrom, a patient's chair having a seat and positioned adjacent said base and outward from said post, an elongated table supported upon the top of said frame, electrical power means connected to the seat of said chair and operable to elevate said seat toward said frame, an electrical circuit connected between said electrical power means and a source of electric current, a safety switch in said circuit, and an actuating member for said safety switch supported by said frame in a position to be engaged by the lap or thighs of a patient when seated in said chair and operable to open said safety switch to discontinue further elevation of said chair when said actuating member is engaged by the lap or thighs of said patient.

4. The support according to claim 3 in which said actuating member extends horizontally beneath said frame a predetermined distance in spaced relation to the lower portion of said frame, and further including spring means positioned between said actuating member and frame and operable thereby to maintain said safety switch open.

5. The support according to claim 4 further characterized by said actuating member comprising an elongated plate-like member.

* * * * *